US00PP34165P2

(12) United States Plant Patent
Slaughter et al.

(10) Patent No.: US PP34,165 P2
(45) Date of Patent: Apr. 26, 2022

(54) NECTARINE TREE NAMED 'WANECTSIX'

(50) Latin Name: *Prunus persica nucipersica*
Varietal Denomination: Wanectsix

(71) Applicant: Wawona Packing Co., LLC, Cutler, CA (US)

(72) Inventors: John Keith Slaughter, Fresno, CA (US); Kaylan M. Roberts, Fresno, CA (US)

(73) Assignee: Wawona Packing Co., LLC, Cutler, CA (US)

( * ) Notice: Subject to any disclaimer, the term of this patent is extended or adjusted under 35 U.S.C. 154(b) by 0 days.

(21) Appl. No.: 17/300,762

(22) Filed: Oct. 26, 2021

(51) Int. Cl.
*A01H 5/08* (2018.01)
*A01H 6/74* (2018.01)

(52) U.S. Cl.
USPC ..... Plt./190
CPC ..... *A01H 6/7454* (2018.05)

(58) Field of Classification Search
USPC ..... Plt./190
CPC ..... A01H 5/0856
See application file for complete search history.

(56) References Cited

U.S. PATENT DOCUMENTS

PP7,506 P 4/1991 Bradford et al.
PP21,724 P2 2/2011 Slaughter et al.

*Primary Examiner* — Kent L Bell
(74) *Attorney, Agent, or Firm* — Potter Anderson & Corroon LLP

(57) ABSTRACT

A new and distinct variety of nectarine tree (*Prunus persica nucipersica*), which is denominated varietally as 'Wanectsix', and which produces an attractively colored yellow-fleshed, large sized, low acid, clingstone nectarines which is mature for harvesting and shipment approximately July 20 to July 30 under the ecological conditions prevailing in the San Joaquin Valley of central California.

1 Drawing Sheet

Botanical Designation: *Prunus persica nucipersica.*
Varietal Denomination: 'Wanectsix'.

BACKGROUND OF THE NEW VARIETY

The present variety of nectarine tree resulted from an on-going program of fruit tree breeding. The purpose of this program is to improve the commercial quality of deciduous fruit varieties and rootstocks by creating and releasing promising selections of *Prunus* species. To this end, both controlled and hybrid cross pollinations are made each year to produce seedling populations from which improved progenies are evaluated and selected.

The seedling, 'Wanectsix' was originated by the breeders and selected from a population of seedlings growing in experimental orchards located near Fowler, Calif. The seedlings, grown on their own roots, were derived from planting seed of the 'M15.142' nectarine seedling (un-patented), which was used as the female parent. The pollen parent was from a different nectarine selection designated as 'E45.013' (U.S. Plant Pat. No. 21,724). The resulting fruit was collected from the female parent at a mature stage, and seeds were extracted in July of 2009. After a period of stratification, the seed was placed in the greenhouse by population and then field planted for tree establishment and, ultimately, to exhibit fruit for evaluation. One yellow-fleshed nectarine seedling, which is the present variety, exhibited especially desirable characteristics, and was then designated as 'H6.219'. This seedling was marked for subsequent observation. After the 2013 fruiting season, the new variety of nectarine tree was selected for advanced evaluation and repropagation.

ASEXUAL REPRODUCTION

Asexual reproduction of this new and distinct variety of nectarine tree was accomplished by budding the new nectarine tree onto 30 trees of 'Nemaguard' Rootstock (un-patented). This was performed by the breeders in an experimental orchard, which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF VARIETY

'Wanectsix' is a new and distinct variety of nectarine tree, which is considered of large size, and which has a vigorous growth characteristic. This new tree is also a regular and productive bearer of relatively large, firm, yellow-fleshed, low acid, clingstone fruit which have very good flavor and eating qualities.

This new nectarine tree has a medium chilling requirement of approximately 500 hours, and further produces relatively uniformly sized fruit throughout the tree's canopy. In addition to the foregoing, the fruit of the new nectarine also appears to have good handling and shipping qualities. The 'Wanectsix' nectarine tree bears fruit which are typically ripe for commercial harvesting and shipment on approximately July 20 to July 30 under the ecological conditions prevailing in the San Joaquin Valley of central California. In relative comparison to the 'Summer Fire' nectarine tree (U.S. Plant Pat. No. 7,506), which is the closest known variety, the current variety of nectarine tree bears fruit that exhibit a lower and more moderate flesh acidity and is 5.0 mm to 7.0 mm larger than comparator variety when grown under the same conditions and fruit numbers per tree. In relative comparison to the un-patented nectarine seed parent tree ('M15.142'), the current variety exhibits yellow-flesh which is contrasted to the seed parent that exhibits white-fleshed fruit. Additionally, the current variety exhibits a higher concentration of red surface blush on the fruit skin surface. In comparing the current variety to its nectarine pollen parent, the current variety ripens approximately 35 days after the pollen parent ('E45.013', U.S. Plant Pat. No. 21,724).

BRIEF DESCRIPTION OF THE DRAWINGS

FIG. 1 is a color photograph of three whole mature fruit harvested, from a fifth leaf year tree, displaying both the apical and basal fruit aspects and one mature fruit from which a sagittal wedge has been cut and placed beside the donor fruit, which reveals the internal flesh color and the clingstone characteristics thereof. The external coloration of the fruit as shown in the photograph is sufficiently matured for harvesting and shipment. The colors in these photographs are as nearly true as is reasonably possible in a color representation of this type. Due to chemical development, processing and printing, the leaves and fruit depicted in these photographs may, or may not, be accurate when compared to the actual specimen. For this reason, future color references should be made to the color plates (Royal Horticultural Society, Fourth Edition, 2001) and descriptions provided, hereinafter.

NOT A COMMERCIAL WARRANTY

The following detailed description has been prepared to solely comply with the provisions of 35 U.S.C. § 112, and does not constitute a commercial warranty (either expressed or implied) that the present variety will in the future display all the botanical, pomological or other characteristics as set forth hereinafter. Therefore, this disclosure may not be relied upon to support any future legal claims including, but not limited to, breach of warranty of merchantability, or fitness for any purpose, or non-infringement which is directed, in whole, or in part, to the present variety.

DETAILED DESCRIPTION

Referring more specifically to the pomological details of this new and distinct variety of nectarine tree, the following has been observed during the tenth fruiting season, and under the ecological conditions prevailing at the orchards of the assignee which are located near the town of Fowler, county of Fresno, state of California. All major color code designations are by reference to The RHS Colour Chart (Royal Horticultural Society, Fourth Edition, 2001) provided by The Royal Horticultural Society of Great Britain. Common color names are also occasionally used.

TREE

Size: Generally considered medium-large in its growth pattern as compared to other common commercial nectarine cultivars ripening in the late season of maturity. The tree of the present variety was pruned to a height of about 270.0 cm to about 310.0 cm at commercial maturity. Fruit size can vary with crop load and the conditions under which the fruit and tree are grown.

Width: About 265.0 cm.

Vigor: Considered moderately vigorous. The present nectarine tree variety grew from about 175.0 cm to about 180.0 cm in height during the first growing season. The new variety was pruned to a height of about 150.0 cm during the first dormant season, and primary scaffolds were then selected for the desired tree structure.

Productivity: Productive. Fruit sets are generally more than the desired crop. Preharvest fruit thinning is required when the new variety is grown in a suitable horticultural zone, and under appropriate commercial nursery conditions. The fruit set is spaced by thinning to develop the remaining fruit into the desired market-sized fruit. The number of the fruit set varies with the prevailing climatic conditions, and the cultural practices employed.

Fruit bearing: Regular. Fruit set has been more than adequate during the previous years of observation, and thinning was necessary during the past 8 years on both the original seedling and on subsequent asexually reproduced trees.

Tree form: Upright and pruned into a vase shape.

Density: Considered moderately dense.

Hardiness: The present tree was grown and evaluated in USDA Hardiness Zone 9. The calculated winter chilling requirements of the new tree is approximately 500 hours at a temperature below 7.0 degrees C.

The present variety appears to be hardy under typical central San Joaquin Valley climatic conditions.

TRUNK

Diameter: About 22.0 cm in diameter when measured at a distance of approximately 15.5 cm above the soil level. This measurement was taken at the beginning of the 8th growing season.

Bark texture: Considered moderately rough, with folds of papery scarfskin being present.

Lenticels: Numerous flat, oval lenticels are present. The lenticels range in size from about 4.0 mm to about 7.0 mm in width, and between about 1.0 mm and about 3.0 mm in height.

Lenticel color: Considered an orange brown (RHS Greyed-Orange Group 167 A).

Bark coloration: Variable, but it is generally considered to be a greyed tan (RHS Greyed-Orange Group 176 B).

BRANCHES

Size: Considered medium large for the variety.

Diameter: Average as compared to other nectarine varieties. The branches have a diameter of about 16.0 cm when measured during the 8th year after grafting.

Flowering shoot thickness: Average for the species. About 7.0 mm to 15.0 mm.

Surface texture: Relatively smooth.

Crotch angles: Primary branches are considered variable and are usually growing at an angle of about 50.0 degrees when measured from a horizontal plane.

Current season shoots: Surface texture-Substantially glabrous.

Internode length: Approximately 3.0 cm.

Color of mature branches: Approximately Grey brown (RHS Greyed-Orange Group 177 C).

Current season's shoots: Color.-Light green (RHS Yellow-Green Group 145 B). The color of new shoot tips is considered a bright and shiny green (RHS Yellow-Green Group 146 D).

LEAVES

Size: Considered moderately large and narrow for the species. Leaf measurements have been taken from vigorous, upright, current-season growth, at approximately mid-shoot.
Leaf length: About 178.0 mm to about 183.0 mm (including the petiole).
Leaf width: About 41.0 mm to about 47.0 mm.
Leaf base-shape: The leaves generally exhibit equal marginal symmetry relative to the leaf longitudinal axis.
Leaf form: Lanceolate.
Leaf tip form: Acuminate.
Leaf color: Upper Leaf Surface-Medium green (approximately RHS Green Group 137 B).
Leaf texture:
*Upper leaf surface.*—Glabrous.
*Lower leaf surface.*—Glabrous.
Leaf color: Lower Leaf Surface-Medium green (approximately RHS Green Group N138 B).
Leaf venation: Pinnately veined.
Mid-vein: Color-Considered a pale green (approximately RHS Yellow-Green Group 145 A).
Leaf margins: Gently undulating.
*Form.*—Considered crenulate.
*Uniformity.*—Generally uniform.
Leaf petioles:
*Form.*—Considered canaliculated. The petiole margin is considered rounded when viewed from the ventral aspect.
*Size.*—Considered medium-small for the species.
*Length.*—About 7.0 to about 10.0 mm.
*Diameter.*—About 1.5 to about 2.0 mm.
*Color.*—A yellowed green, (approximately RHS Yellow-Green Group 145 A).
*Texture.*—Glabrous.
*Strength.*—Durable for species until senescence.
Leaf glands:
*Size.*—Considered relatively small for the species; approximately 2.0 mm. in width; and about 2.0 mm. in height.
*Number.*—Generally, one and less common two glands appear per marginal side are found.
*Type.*—Glands reniform in shape.
*Color.*—Considered a yellowed green, approximately (RHS Yellow-Green Group 146 C).
Leaf stipules:
*Size.*—Medium for this variety.
*Length.*—About 5.0 mm to about 7.0 mm.
*Width.*—About 1.0 mm.
*Number.*—Typically, 2 per leaf bud, and up to 6 per shoot tip.
*Form.*—Lanceolate in form and having a serrated marginal edge.
*Color.*—Green (approximately RHS Yellow-Green Group N145 C) The leaf stipules are generally considered to be early deciduous.

FLOWER BUDS

Hardiness: No winter injury (bud death) has been noted during the last several years of observation in the central San Joaquin Valley. The new variety of nectarine tree has not been intentionally subjected to drought, cold or heat stress, and therefore this information is not available.
Flower bud: Size-Variable, and dependent on the state of maturity. The flower buds as described were observed approximately 7 days prior to bloom.
*Length.*—About 16.5 mm.
*Diameter.*—About 9.5 mm.
*Surface texture.*—Pubescent.
*Orientation.*—Considered appressed but appear less so as the blossoms near opening.
Bud scale color: Approximately RHS Greyed-Orange Group 175 A.

FLOWERS

Date of first bloom: Observed on Feb. 21, 2018.
*Blooming time.*—Considered average to slightly early mid-bloom in relative comparison to other commercial nectarine cultivars grown in the central San Joaquin Valley. The date of full bloom was observed on Feb. 28, 2018. The date of full bloom varies slightly with climatic conditions, and prevailing cultural practices.
*Duration of bloom.*—Approximately 8 or more days. This characteristic varies slightly with the prevailing climatic conditions.
Flower class: Considered a perfect flower, complete and perigynous.
Flower type: The variety is considered to have a showy-type flower.
Flower size: Considered large. The flower diameter at full bloom, is about 37.0 mm to about 42.0 mm.
Bloom quantity: Considered abundant.
Flower bud density: Generally considered dense.
*Flower bud frequency.*—Generally, two flower buds appear per node, occasionally one flower bud per node is observed.
Petal size: Generally considered large for the species.
*Petal length.*—About 18.0 mm to about 20.0 mm.
*Petal width.*—About 13.0 mm to about 15.0 mm.
Petal form: Considered broadly ovate.
Petal count: 5.
Petal texture:
*Upper petal texture.*—Very finely pubescent, satin like.
*Lower petal texture.*—Very finely pubescent, satin like.
Petal color: Considered a light pink at the popcorn stage (RHS Red-Purple Group 65 C).
Fragrance: Slight.
Petal claw:
*Form.*—The claw is considered ovate and is generally large.
*Length.*—About 12.0 mm.
*Width.*—About 10.0 mm.
Petal margins: Generally, slightly undulate.
Petal apex: Entire.
Flower pedicel:
*Length.*—Considered large with an approximate length of about 2.5 mm to about 3.5 mm.
*Diameter.*—About 1.0 mm to about 1.5 mm.
*Color.*—A medium brown (approximately RHS Grey-Brown Group N199 D) depending on pedicel and fruit maturity and timing of visual observance.
*Strength.*—Tenacious. Average for the species.
*Texture.*—Generally smooth to slightly undulate.

Floral nectaries:
*Color.*—Considered a pale yellow (approximately RHS Greyed-Orange Group N163 D).
Calyx:
*Surface texture.*—Finely pubescent.
*Color.*—Approximately RHS Greyed-Red Group 178 B.
Sepals:
*Upper surface texture.*—Moderately pubescent.
*Lower surface texture.*—Glabrous.
*Number.*—5 sepals.
*Size.*—Considered medium.
*Sepal length.*—About 4.0 mm to about 6.0 mm.
*Sepal width.*—About 4.5 mm to about 6.0 mm.
*Sepal shape.*—Generally obovate.
*Sepal margin.*—Considered smooth and entire.
*Sepal color.*—A pale green. Approximately RHS Green Group 138 B.
Anthers:
*Generally.*—Average in size.
*Color.*—Yellow-gold when viewed dorsally and prior to dehiscence (approximately RHS Greyed-Orange Group 163 B).
*Position relative to stigma.*—Generally, the stigma is superior to the anthers by about 1.0 mm.
Pollen production: Pollen is abundant and has a yellow color (approximately RHS Yellow-Orange Group 17 C).
Fertility: Self-fertile.
Filaments:
*Size.*—About 15.0 mm to about 18.0 mm in length.
*Color.*—Considered white to a pinkish white (RHS White Group N155 C).
Pistil:
*Number.*—Usually one, and only rarely more than one.
*Generally.*—Considered medium in size.
*Length.*—About 18.0 mm to about 20.0 mm in length including the ovary.
*Width.*—About 1.5 mm.
*Depth.*—About 2.0 mm.
*Color.*—Considered a very pale green (approximately RHS Yellow-Green Group 150 D).
*Surface texture.*—The variety has a long glabrous pistil.
*Position relative to petals.*—At flower maturity the stamens grow to be superior to the petals.
*Ovary surface texture.*—Glabrous.

FRUIT

Maturity when described: Firm ripe condition (shipping ripe).
Date of first picking: Approximately Jul. 20, 2021.
Date of last picking: Approximately Jul. 30, 2021.
Size: Generally-Considered medium large.
Average cheek diameter: About 84.0 mm to about 92.0 mm.
Average axial diameter: About 80.0 mm to about 85.0 mm.
Typical weight: About 285.0 grams.
Fruit soluble solids. Approximately 15.0-20.0 Brix.
Fruit firmness: Fruit flesh pressures generally averaged 14.0 pounds at the time the fruit was analyzed.
Titratable acidity: Approximately 0.35 to 0.42 at commercial harvest maturity.
Fruit form: Generally-Considered slightly drupe shape. When viewed from the basal aspect, both hemispheres of the suturial plane can be extended giving some fruits a slight triangular appearance. The fruit is generally very uniform in symmetry.
Mucron tip: Absent.
Fruit suture: Smooth and uniform. No stitching exists along the suture line.
Suture: Color-Generally, the fruit appears blushed to the same degree as the skin (approximately RHS Orange-Red Group N34 A).
Ventral surface: Form-Considered even, and uniform in appearance, when it is viewed from the lateral, sutural plane.
Apex: Shape-Rounded to slightly retuse.
Base: Shape-Generally smooth.
Stem cavity: Generally-It extends in a rounded circular form which is generally considered uniform. The stem cavity is rounded and relatively deep. The average depth of the stem cavity is about 10.0 mm to about 16.0 mm. The average width of the stem cavity is about 18.0 mm. The average length of the stem cavity, when measured in the suturial plane, is about 22.0 mm.
Fruit skin:
*Thickness.*—Considered medium in thickness, and tenacious to the flesh.
*Surface texture.*—Glaborous.
*Conspicuousness of lenticels.*—Very few.
*Taste.*—Non-astringent.
*Tendency to crack.*—Not observed in the previous years of observation and evaluation.
Fruit skin color:
*Blush color.*—Generally speaking, a red blush exists on much of the skin of the fruit (approximately RHS Red Group 46 B).
Ground color: A medium yellow-gold (approximately RHS Group-Yellow-Orange 17C).
Fruit glossiness: Fruit considered to be medium glossy.
Fruit stem:
*Size.*—Relatively long in length, about 6.0 mm to about 9.0 mm.
*Diameter.*—About 2.0 mm to about 3.0 mm.
*Color.*—Pale yellow green (approximately RHS Yellow-Green Group N144 C).
Fruit flesh:
*Ripening.*—Considered even.
*Texture.*—Firm, juicy and dense. Considered non-melting in flesh classification.
*Fibers.*—Present but not prominent.
*Aroma.*—Slight.
*Eating quality.*—Considered very good.
*Flavor.*—Considered balanced with sweetness and medium acidity.
*Juice production.*—Moderate.
*Brix.*—About 14.0 to 20.0 degrees.
*Acidity.*—Considered medium. Approximately 0.4 titratable acidity at fruit harvest.
*Flesh color.*—It is considered a medium yellow (approximately RHS Yellow-Orange Group 14 C).

STONE

Type: Considered a clingstone.
Size: It is generally considered to be medium large for the species.
Length: Average, about 37.0 mm to about 40.0 mm.
Width: Average, about 22.0 mm to about 26.0 mm.

Diameter: Average, about 17.0 mm to about 21.0 mm.
Form: Roughly ovoid.
Stone base: Shape-The stone is considered shortly attenuate.
Apex: Shape-The stone exhibits a very slight acute apex.
Stone surface:

*Surface texture.*—Considered irregularly furrowed toward the apex. Further, more pitting exists in nearly all portions of the stone and is more common toward the base and ventral edges.

*Ridges.*—Ridging is generally more prominent, and is usually oriented parallel, at the dorsal margins.

*Ventral edge.*—The ventral edge is generally described as having adjoining ridges formed from each hemisphere.

*Dorsal edge.*—Shape-Generally considered even. The folds of the surface ridges appearing on the external margins often end gently along the suture.

Stone color: The color of a mature, dry stone is generally considered a light tan (approximately RHS Greyed-Orange Group 170 C).
Tendency to split: Splitting has rarely been noted.
Kernel:

*Length.*—About 16.0 mm to about 19.0 mm.

*Width.*—About 12.0 mm to about 15.0 mm.

*Thickness.*—About 4.0 mm to about 6.0 mm.

*Size.*—The kernel is considered medium to large in size.

*Form.*—Considered generally ovoid.

*Kernel surface texture.*—Kernel pellicle is shortly pubescent.

*Color.*—A dark tan (RHS Greyed-Orange Group 165 C).

Use: The present variety 'Wanectsix' is a nectarine tree of the late season of maturity, and which produces fruit which are firm, attractively colored, and which are useful for both local and long-distance shipping.
Keeping quality: Appears excellent. The fruit of the present variety has stored well for periods of up to 30 days after harvest at 1.0 degree Celsius.
Shipping quality: Good. The fruit of the new nectarine tree variety showed minimal bruising of the flesh or skin damage after being subjected to normal harvesting and packing procedures.
Resistance to insects and disease: No susceptibilities were noted. The present variety has not been intentionally tested to expose or detect any susceptibilities or resistances to any known plant, fruit diseases, insect, frost, winter injury or other environmental factors.

Although the new variety of nectarine tree possesses the described characteristics when grown under the ecological conditions prevailing near Fowler, Calif., in the Central part of the San Joaquin Valley of California, variations of the usual magnitude, and characteristics incident to changes in growing conditions, fertilization, nutrition, pruning, pest control, frost, climatic variables and changes in horticultural management are to be expected.

Having thus described and illustrated our new variety of nectarine tree, what we claim is new, and desire to secure by plant Letters Patent is:

1. A new distinct variety of nectarine tree substantially as illustrated and described, and which is characterized principally as to novelty by producing an attractively colored yellow-fleshed, large sized, low acid, clingstone nectarine which is mature for harvesting and shipment approximately July 20 to July 30 under the ecological conditions prevailing in the San Joaquin Valley of central California.

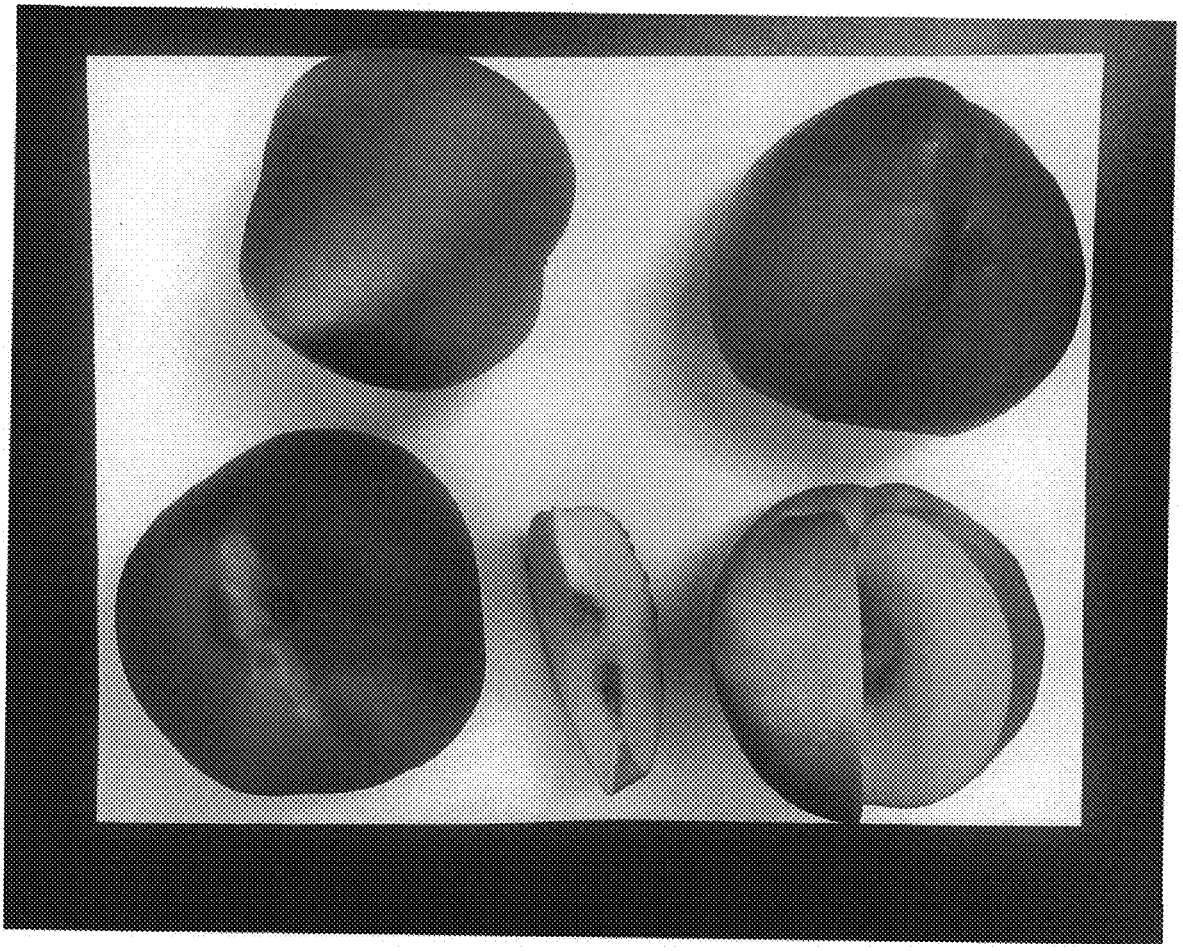

* * * * *